United States Patent [19]
Platzker

[11] Patent Number: 5,313,942
[45] Date of Patent: May 24, 1994

[54] ELECTRODE SYSTEM AND METHOD FOR EKG TESTING

[76] Inventor: Yakov Platzker, 90 Hayarden St., Ramat Gan, Israel

[21] Appl. No.: 885,374

[22] Filed: May 19, 1992

[30] Foreign Application Priority Data

May 20, 1991 [IL] Israel .......................................... 98188

[51] Int. Cl.⁵ .............................................. A61B 5/02
[52] U.S. Cl. .................................... 128/639; 128/707; 607/77
[58] Field of Search .............................. 128/639-644, 128/696-707, 670, 672; 607/77

[56] References Cited

U.S. PATENT DOCUMENTS

| | | | |
|---|---|---|---|
| 3,043,291 | 7/1960 | Nielsen | 128/639 |
| 3,744,480 | 7/1973 | Gause et al. | 128/707 |
| 3,982,529 | 9/1976 | Sato | 128/641 |
| 4,202,344 | 5/1980 | Mills et al. | 128/644 |
| 4,285,515 | 8/1981 | Gezari | 128/707 |
| 4,372,551 | 2/1983 | Yurdin | 128/707 |
| 4,494,552 | 1/1985 | Heath | 128/696 |
| 4,905,705 | 3/1990 | Kizakevich et al. | 128/696 |

FOREIGN PATENT DOCUMENTS

0329306  2/1989  European Pat. Off. ............ 128/639

Primary Examiner—Stephen C. Pellegrino
Assistant Examiner—M. Peffley
Attorney, Agent, or Firm—Edward Langer

[57] ABSTRACT

An electrode system for use in administering an EKG test, provided as a chair with a flexible strap having electrodes embedded therein. The flexible strap is attached to the chair back rest and is tightened around the chest when the patient is seated in the chair. Electrodes fitted in the lower portion of the chair and the armrest make connection, respectively, to the legs and arms, thereby completing the test set-up procedure in a short time period. The electrodes embedded in the flexible strap are adjustable horizontally, and the strap itself is adjustable vertically, so that particular locations on the chest are reachable, making the strap suitable for all size patients. The chair is designed to become a bed to increase patient comfort. A set of exercise accessories is removably attachable to the chair, to permit EKG measurements during physical exertion. The electrode system has many applications, in hospitals, clinics, emergency rooms, intensive care units, cardiology units, health institutes, old age homes, and sports medicine clinics.

18 Claims, 8 Drawing Sheets

ELECTRODE SYSTEM AND METHOD FOR EKG TESTING

FIELD OF THE INVENTION

The present invention relates to medical diagnostic electrode devices for use with diagnostic instruments such as an EKG, and more particularly, to a set of EKG electrodes arranged to minimize the required set-up time before commencing the test.

BACKGROUND OF THE INVENTION

The prior art of medical diagnostic electrodes includes a set of electrodes for application to the body skin for purposes of performing an EKG test. Individual ones of these electrodes are applied by a medical assistant to the limbs and the chest of the patient, and this requires a certain set-up time in preparation for the test. The electrodes are attached to cables which often become entangled, making identification of the proper electrode difficult as well as consuming additional set-up time.

The set-up difficulties with the electrodes and time consuming nature of the activity in performing an EKG test tend to make the patient uncomfortable, and the experience unpleasant.

U.S. Pat. No. 4,706,679 to Blackham et al. discloses an adjustable head set for use in performing an EEG test, with the head set held in place on the back of a patient's head when the patient leans back against a chair head rest. The head set includes disposable monitors which provide good contact with the head without prior skin preparation. This design is not applicable to EKG testing.

U.S. Pat. No. 4,320,768 to Golab et al. discloses an integrated medical testing system for automated administration of test stimuli to a patient, including stimulation control means for automatically administering the stimuli and for controlling a rotatable chair in which the patient is seated.

A set of electrodes for stimulating regions of the skin of disabled individuals is disclosed in U.S. Pat. No. 4,727,878 to Levine, and an example is presented using the electrodes in a wheelchair seat, to avoid the likelihood of pressure sores.

The increase in sophistication of medical instrumentation has led to the development of self-administered test devices for monitoring personal health, such as blood pressure. Designed especially for simplicity of use, such machines are available for public use in shopping centers, etc. Despite these developments, use of the EKG machine remains complicated and time-consuming due to the electrode set-up time.

It would therefore be desirable to provide an electrode system to facilitate use of the EKG machine quickly and easily.

SUMMARY OF THE INVENTION

Accordingly, it is a principal object of the present invention to overcome the above-mentioned disadvantages and provide an electrode system and method of use for EKG testing, to simplify the set-up procedure by requiring less trained personnel and reducing the set-up time involved.

In accordance with a preferred embodiment of the invention, there is provided an electrode system for reducing the set-up time in medical diagnostic testing (EKG) comprising in combination:

support structure means for supporting the body;

a first plurality of electrodes supported by said support structure means; and a second plurality of electrodes each fixedly mounted at a location on said support structure means, such that when the body is supported by said support structure means, said first and second plurality of electrodes contact the body and enable rapid electrical connection thereto for diagnostic testing.

In the preferred embodiment, the inventive electrode system comprises a chair designed for use in administering an EKG test, with a flexible strap having electrodes embedded therein. The flexible strap is attached to the seat back rest and is tightened around the chest when the patient is seated in the chair. Electrodes fitted in the lower portion of the chair and the armrest make connection, respectively, to the legs and arms, thereby completing the set-up procedure in a short time period.

The electrodes embedded in the flexible strap are adjustable horizontally, and the strap itself is adjustable vertically, so that particular horizontal locations on the chest are reachable, making the strap suitable for all size patients.

The chair is preferably designed with the ability to recline and become a bed, to increase patient comfort when needed. A set of exercise accessories is easily and removably attached to the chair to permit EKG measurements of the patient during physical exertion, while seated or reclining.

A feature of the electrode system is the use of a single cable multi-wire connection to the chair via a plug-in receptacle, enabling a quick and simple connection of the electrodes to the EKG machine.

The advantages of the inventive system over the prior art include the significant reduction in set-up time for EKG tests, in addition to reducing the likelihood of connection errors. The electrode strap connection to the chest is more secure, without the need to shave body hair as is often needed with prior art using rubber suction cups. This also improves the quality of the connection and reduces extraneous indications.

The electrode strap also reduces electrode wire breakage upon repeated use. Repeated EKG tests can be quickly and easily performed since the set-up procedure is simplified. The chair design reduces movement problems for the aged or infirm.

The inventive electrode system can be use in many applications in hospitals, medical clinics, emergency rooms, intensive care units, cardiology units, private health institutes, old age homes, and sports medicine clinics.

The inventive electrode system may also be applied to the development of EKG machines for self-administered tests.

Additional electrode system arrangements are possible, such as electrodes which are vertically-oriented for body contact.

Other features and advantages will become apparent from the drawings and the description contained hereinbelow.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF THE PREFERRED EMBODIMENTS

Figure 1A:
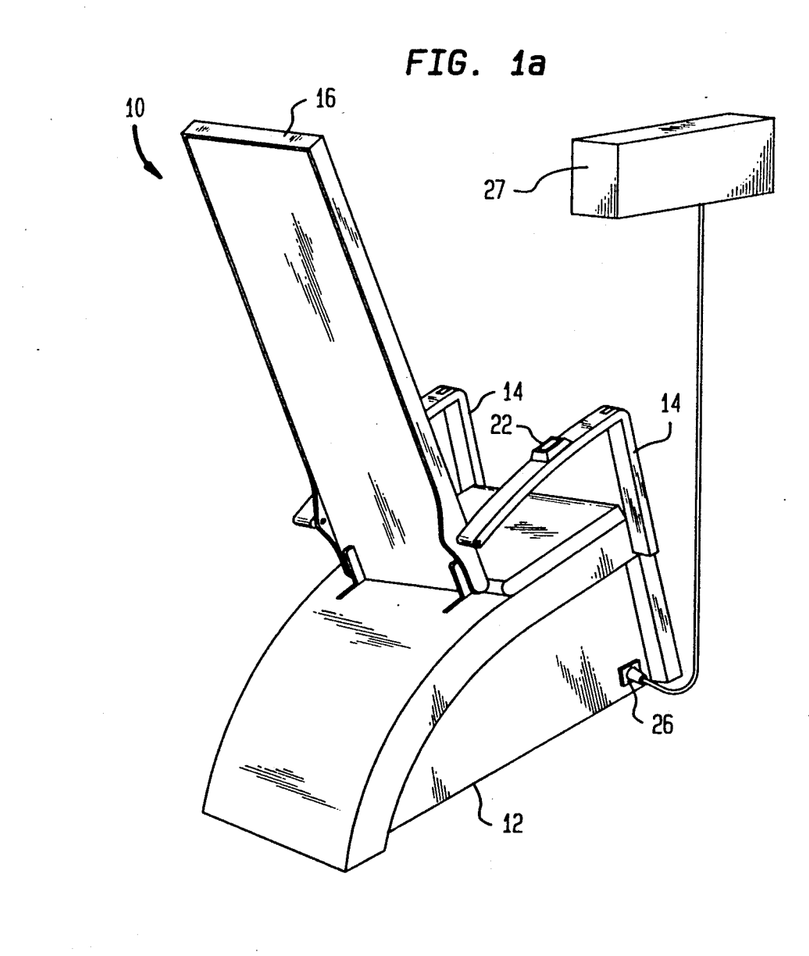
FIGS. 1a-b are, respectively, front and rear perspective views of an electrode system for EKG testing, constructed in accordance with the principles of the invention.
Figure 1B:
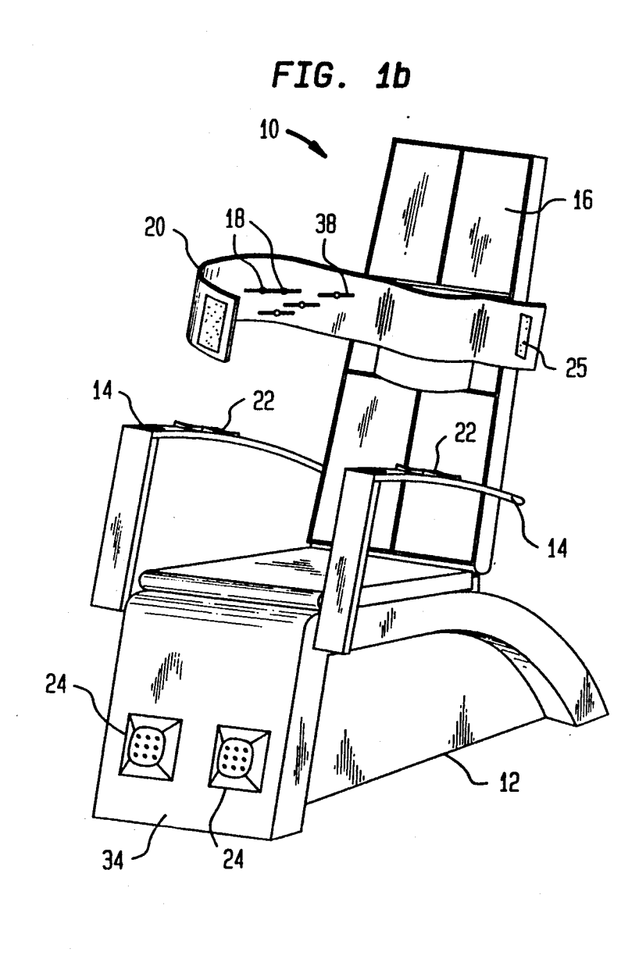

Referring now to FIGS. 1a-b, there are shown, respectively, front and rear perspective views of an electrode system arranged in a chair 10 for use in performance of EKG tests. Chair 10 comprises a base 12, a pair of arm rests 14, and a seat back 16. The electrode system comprises electrodes 18 embedded in a flexible strap 20 attached to seat back 16, and a set of fixed electrodes 22, 24 mounted respectively, in each of arm rests 14 and base 12. An adhesive clamp 25 is provided to secure the ends of strap 20. A cable receptacle 26 provided in base 12 enables a multi-wire cable connection to EKG machine 27.

Figures 2A, 2B:
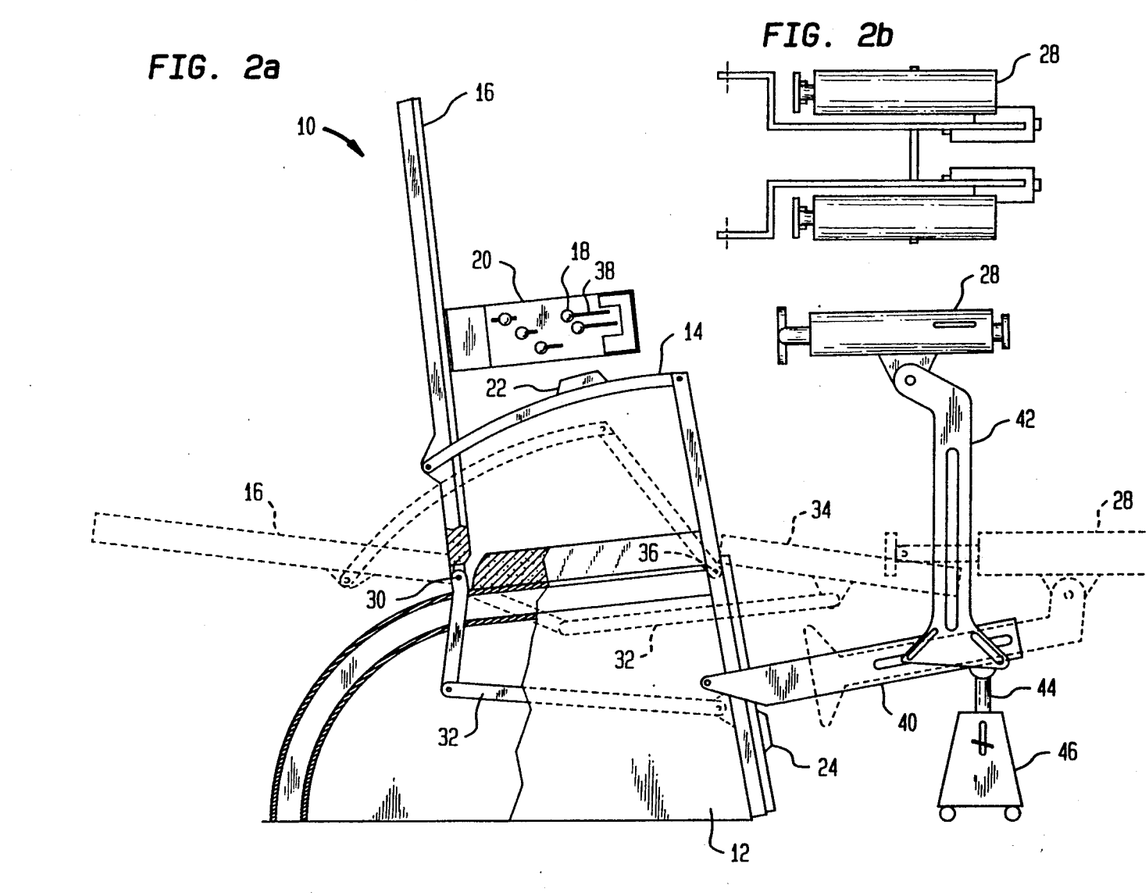
FIGS. 2a-b are, respectively, a side view of the chair containing the electrode system and a top view of an exerciser.

In FIGS. 2a-b there are shown, respectively, a side view of chair 10 containing the electrode system and a top view of an exerciser 28 which may be attached to chair 10 as needed. Chair 10 is designed to be adjustable into normal and reclining positions, allowing the EKG test to be performed in either or both positions. Seat back 16 is pivotable about an axis 30, to which there is attached one end of a foldable brace 32. The other end of brace 32 supports a foot rest 34, pivotable about axis 36. Arm rests 14 pivot about axis 36 when seat back 16 is reclined.

Flexible strap 20 is attached so as to be adjustable vertically along seat back 16, and electrodes 18 are adjustable horizontally by movement within slots 38, enabling the electrodes 18 to be located in optimal fashion for test purposes. As described further herein, the adjustment of electrodes 18 is easily and quickly accomplished, reducing the EKG set-up time. Fixed electrodes 22 and 24 are also shown, for the arms and legs.

As shown in FIG. 2a, exerciser 28 is supported by beams 40, 42 which are adjustable so as to position exerciser 28 for operation by the arms or legs as desired. One end of beam 40 is attached to base 12 of chair 10, and the other end is supported on a pin 44 of a movable stand 46. Pin 44 is vertically adjustable to provide height adjustment of beam 40. Beam 42 supports exerciser 28 when positioned for operation by the arms.

In the embodiment shown, exerciser 28 is a simple piston-type unit which operates against spring tension, for example, to provide resistance against pressure applied by the arms or legs. Thus, the physical exertion by the patient can be used to develop stress test conditions. The provision of a built-in exerciser 28 as shown in FIG. 2a simplifies the performance of such tests, with minimum patient discomfort. It will be appreciated that exerciser 28 may be one of many deigns, including a bicycle pedal unit 48 (FIG. 3b) for the legs. Exerciser 28 is designed with electrodes 49a,b to provide contact with the arms and legs, since fixed electrodes 22 and 24 are not used in this case.

Another important test besides the EKG is an echocardiograph, and one of the difficulties in performing this test under stress is the difficulty of insuring a good connection of the transducer to the chest, so that it does not move while the patient exercises. Electrode strap 20 can be adapted for mounting of a transducer to solve this problem to provide a secure chest connection which remains in place during the test.

Figure 3A:
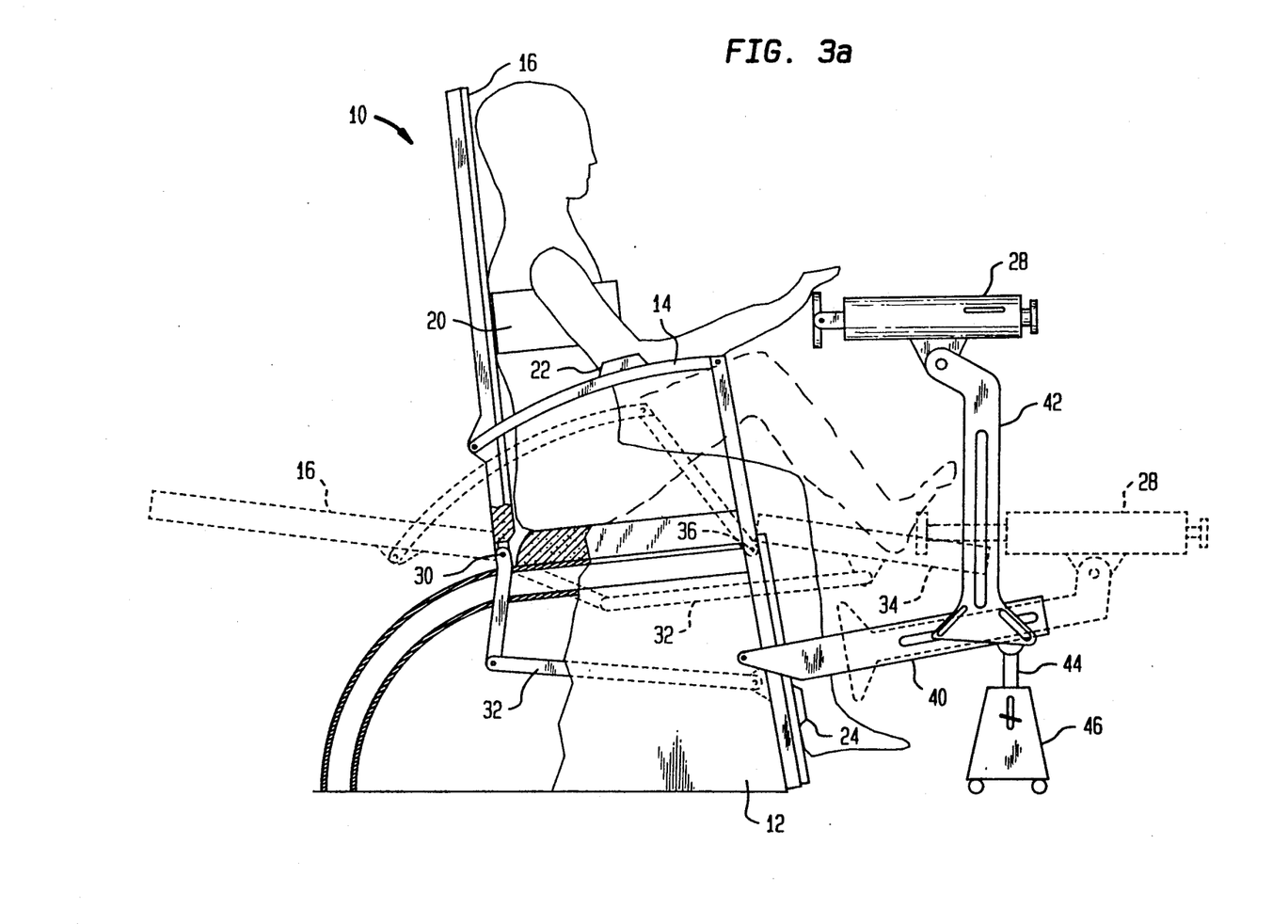
FIGS. 3a-b show a patient seated in the chair of FIGS. 1-2 and ready for EKG testing while using alternative exercisers.
Figure 3B:
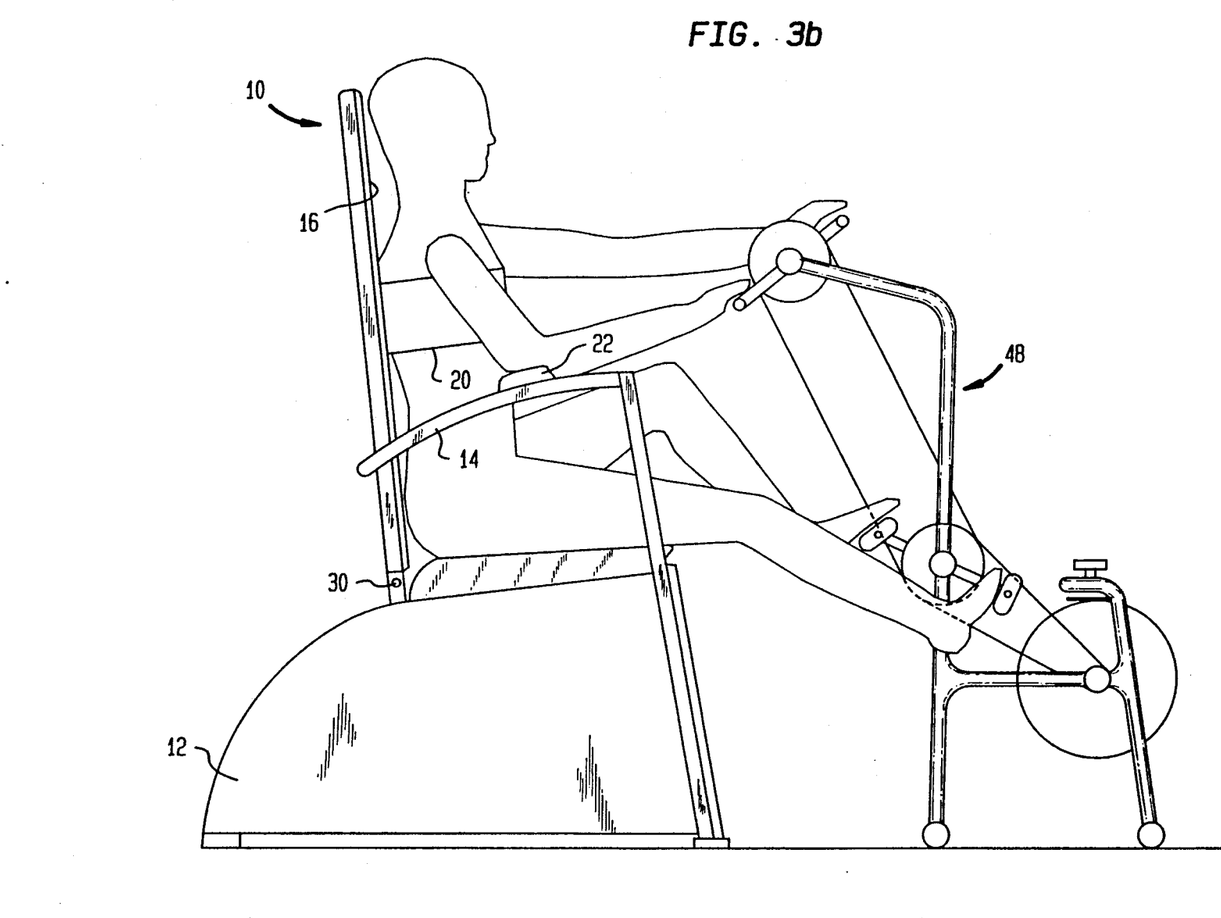

In FIGS. 3a-b, a patient is shown seated in the chair of FIGS. 1-2 and ready for EKG testing during use of exerciser 28 (48). As will be appreciated, exerciser 28 (48) may be removed and a normal EKG testing procedure performed. Once the patient is seated, flexible strap 20 is secured via clamp 25 around the patient's chest, after electrodes 18 have been adjusted for the optimal location. Placement of the patient's arms and legs against fixed electrodes 22, 24 completes the test set-up procedure.

A panel light may be provided on the EKG machine to indicate that contact with the skin has been established. Once the set-up procedure is completed, and cable connections to the EKG machine have been made via receptacle 26, performance of the EKG test proceeds normally. Release of the strap 20 enables the patient to quickly dismount the chair 10 on completion of the test. Repetition of the set-up procedure is then a simple matter once the next patient is seated in chair 10.

Figure 4A:
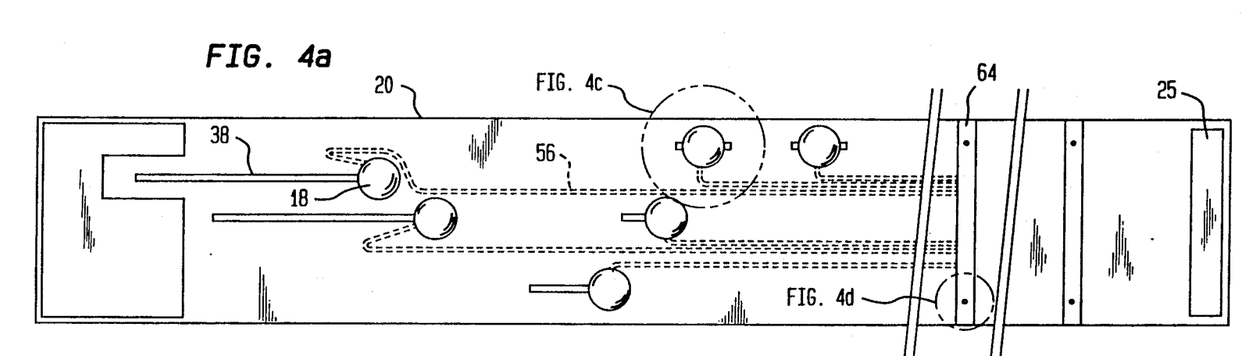
FIGS. 4a-d are, respectively, a front view, an edge view and two enlarged detail views showing the assembly of an electrode strap used in the electrode system of FIGS. 1-3.
Figure 4B:
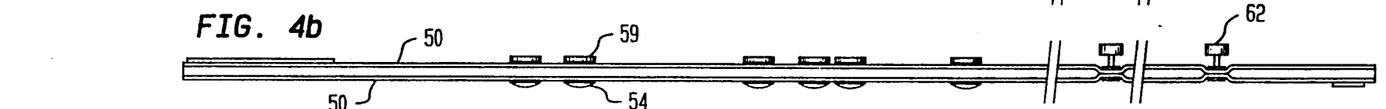
Figure 4C:
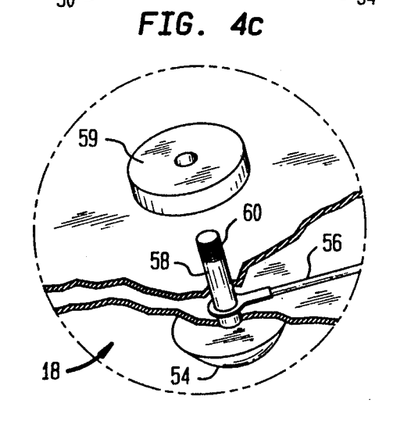

In FIG. 4a, a front view of flexible strap 20 is shown, revealing the mounting arrangement of electrodes 18. Strap 20 comprises a pair of back-to-back layers 50 of electrically insulated material, such as plastic or cloth fabric, having formed therein a plurality of aligned slots 38. An electrode 18 comprising a button-like contact 54 is seated in slot 38 and an electrical connection is made to a wire 56 on a stem 58 extending from contact 54, as shown in the enlarged detail view of FIG. 4c (reversed). Electrode 18 is secured by a threaded washer 59 engaging the threaded portion 60 of stem 58, so that each electrode 18 is slidably adjustable in slot 38, once contact 54 and washer 59 are assembled, as shown in the edge view (FIG. 4b).

Figure 4D:
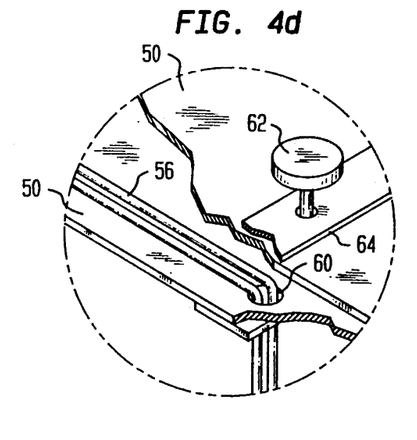

As shown in the enlarged detail view of FIG. 4d, connection wires 56 run between layers 50 of strap 20, until they reach a cable clamp 62 which is provided to tighten against a pair of rigid strips 64 between which strap 20 is clamped. A hole 66 formed through one of layers 50 and strips 64 provides an exit for wires 56, which are connected to receptacle 26 (FIG. 1).

Figure 5A:
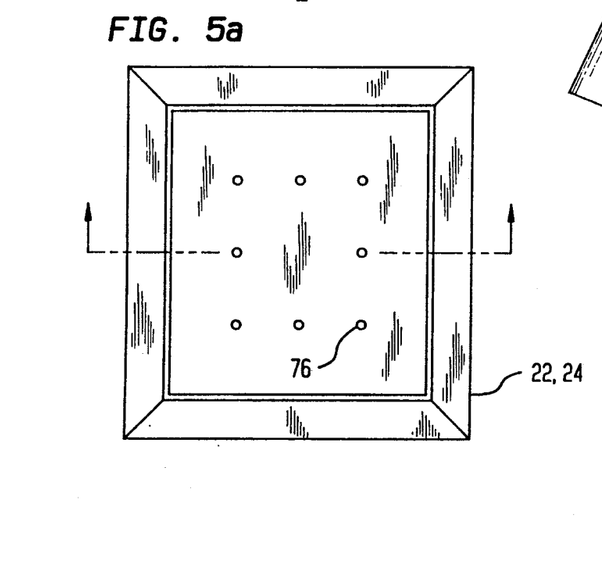
FIGS. 5a-c are, respectively, a top view, a cross-sectional view and a perspective view of an electrode mounted on the chair of FIGS. 1-3.
Figure 5B:
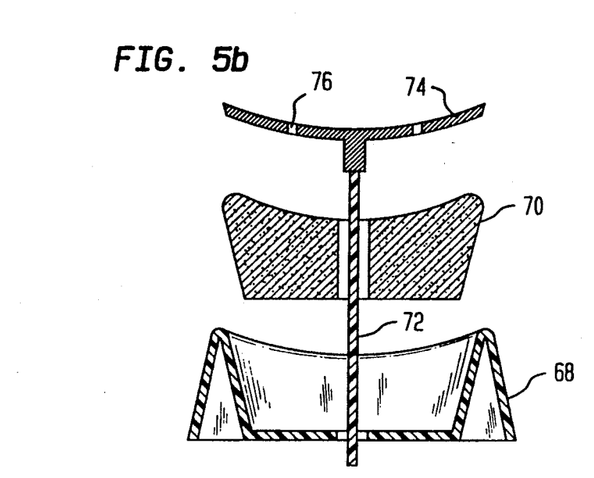
Figure 5C:
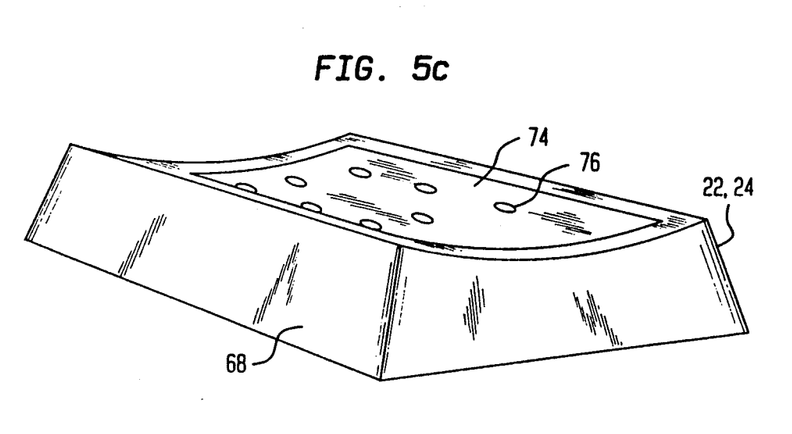

In FIG. 5a, there is shown a top view of electrodes 22 and 24 which are used for connection to the arms and legs. Typically, each of Fixed electrodes 22 and 24 is shaped as a rectangular base 68 containing an absorbent pad 70, through which there passes a wire 72 connected to an electrically-conductive surface 74. Pad 70 contains a conductive liquid, and a plurality of holes 76 are formed in surface 74, to provide contact between the liquid and the skin and insure a good electrical connection. Absorbent pad 70 may be designed for use in electrodes 18. Wire 72 is connected to receptacle 26 for external EKG connection.

It will be appreciated by those skilled in the art that the inventive electrode system can be modified for use in a hospital bed, by attachment of Fixed electrodes 22 and 24 to the bed for connection of the arms and legs. The attachment may utilize quick-release butterfly clamps, enabling placement of electrode strap 20 across the chest, its ends secured by the bed.

It is also possible to add two more electrodes 18 to flexible strap 20, serving as contact for the chest and connected to defibrillator equipment. Thus, if an electrical shock must be administered to correct arrhythmia, these electrodes are already in place, and the shock procedure may be performed more quickly than is normally possible, in life-threatening situations.

Another variation in the design of the inventive electrode system allows the development of an EKG machine for self-administered tests. Thus, chair 10 may be located in a pharmacy or shopping center, and an individual can seat himself in it and connect electrode strap 20 across his chest and the electrodes 22 and 24 to the arms and legs, and then upon depression of a button, the EKG is automatically operated.

Figure 6:
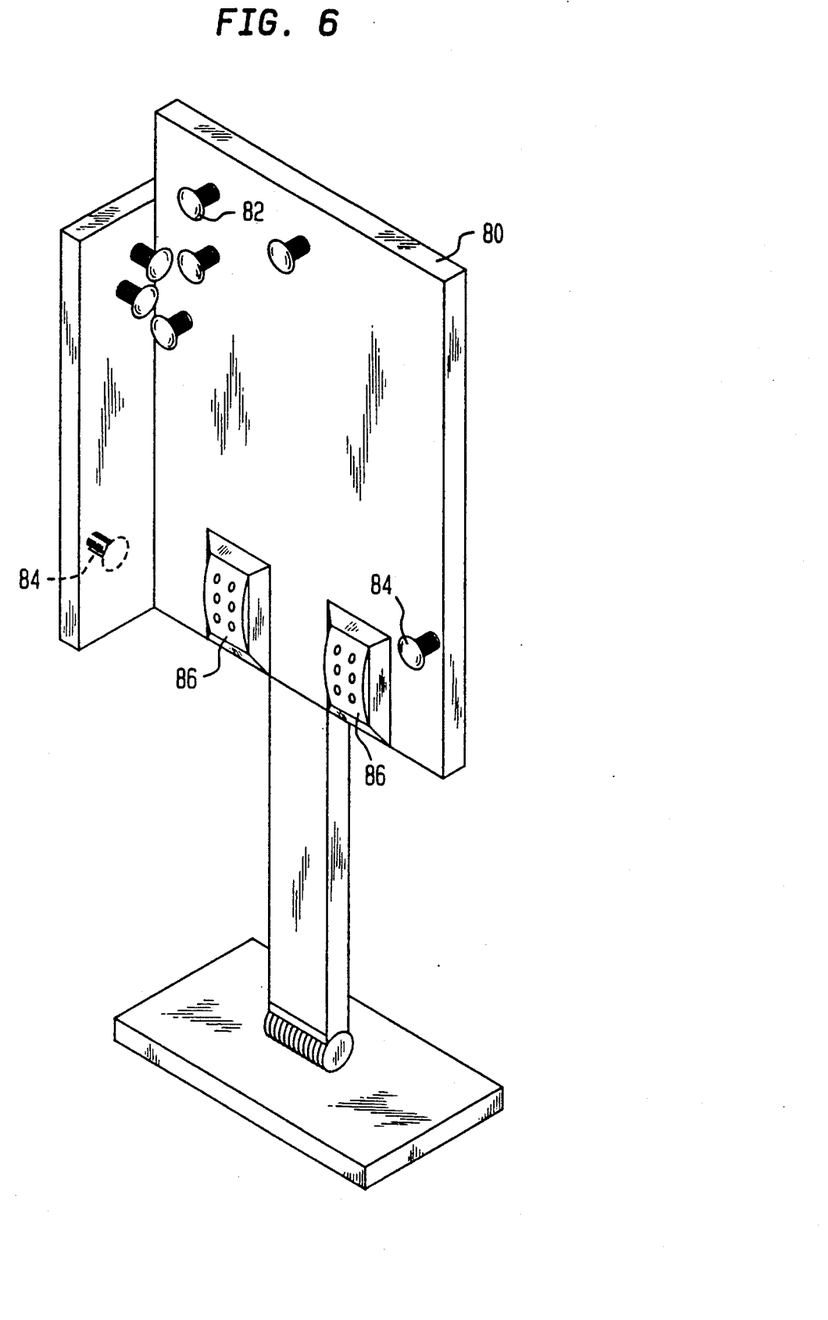
FIGS. 6-7 are perspective views of an alternative embodiment of the invention, featuring an electrode panel for EKG testing.
Figure 7:
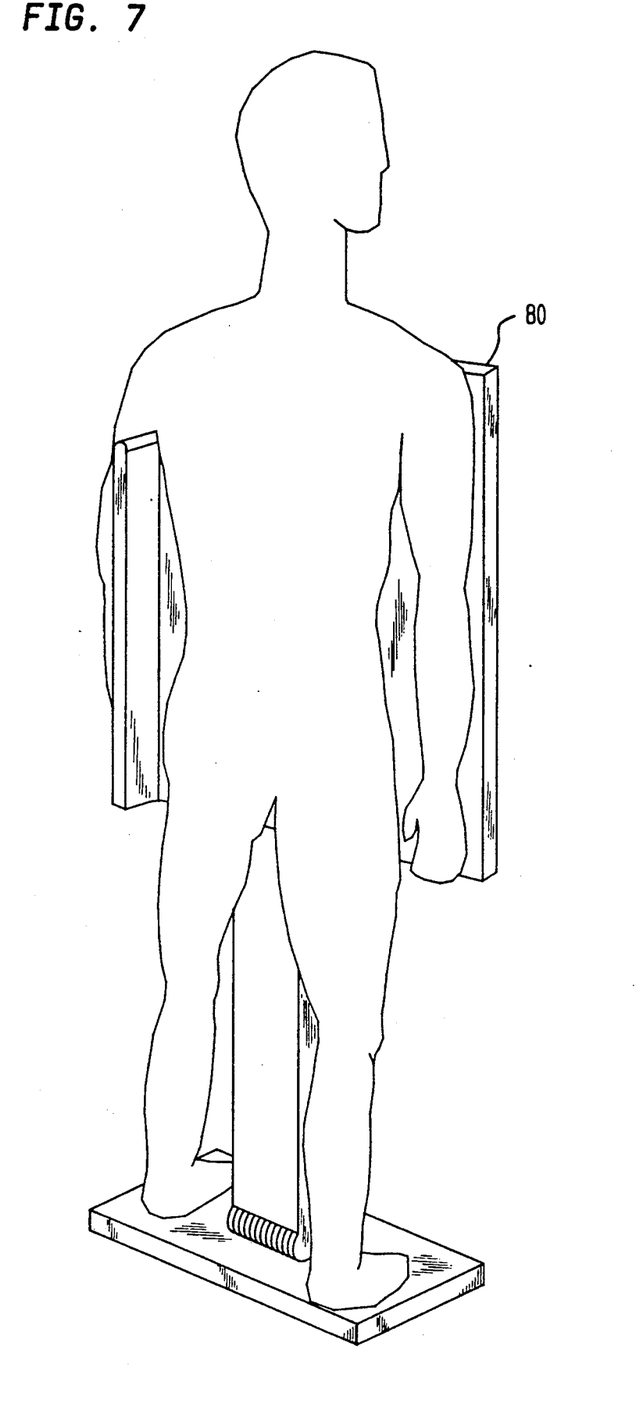

FIGS. 6-7 show perspective views of an alternative embodiment of the inventive electrode system. Instead of a chair and straps, this arrangement comprises a vertical panel 80 on which there are mounted chest, arm and leg electrodes 82, 84, and 86, for placement of the chest, arms and legs so as to make a connection to these electrodes while standing. Typically, panel 80 is slightly tilted, adjustably, toward the body to maintain contact via pressure of the body weight on the electrodes. Again, depression of a button begins the test and provides the results.

The advantages of a self-administered test are many, including the encouragement of more frequent testing by the general public. Even those who consider themselves healthy, and would not schedule an EKG test so as not to convey the impression of health problems, might perform the self-administered EKG test. Those with heart problems and who have regular checkups, might not arrange an EKG test until the next scheduled visit to the doctor. If, in the meantime, these individuals complain about chest pains, etc. the availability of an immediate and easily self-administered EKG test may save the life of such individuals.

In this fashion, repeated tests (as frequent as every two weeks, for example) are easily obtained by such individuals, at reduced cost, and developments are closely monitored in the test results. This enables detection of arrhythmia practically in real-time, since the information is accessible quickly.

A new approach to medical diagnostic testing can be implemented, based on arrangements whereby the self-administered test is performed and the individual provides personal details, name, address, etc., and the machine provides the individual with a receipt containing a number corresponding to the test. The test result itself is transferred immediately, by facsimile, to a medical center where a trained technician reads the result and provides a report, possibly printed on a plastic card, which is mailed to the individual.

In this procedure, if the technician discovers an immediate problem, he or the doctor can telephone the individual and direct him to the nearest hospital emergency room. The advantage in this approach is that the individual arrives at the hospital with the test results reported in previous tests, saving the doctor time in identifying the new findings in comparison to the previous test results. This new approach may be applied in the framework of a medical insurance plan, as it saves on visits to the doctor, and unecessary hospitalization costs, since the comparison of test results can be made immediately in the emergency room before deciding to hospitalize the patient.

Having described the invention with regard to certain specific embodiments, it is to be understood that the description is not meant as a limitation since further modifications may now suggest themselves to those skilled in the art and it is intended to cover such modification as fall within the scope of the appended claims.

I claim:

1. An electrode system for reducing the set-up time for electrode placement on parts of the body in medical diagnostic testing (EKG) comprising in combination:

support structure means for supporting the body;

a first plurality of electrodes supported by said support structure means, wherein said support structure means is a chair for seating the body, and said first plurality of electrodes is enclosed in a flexible strap attached at one end thereof to said chair, for placement of said flexible strap across the chest; and a second plurality of electrodes each fixedly mounted at a location on said chair for contacting the arms and legs, such that when the body is supported by said chair, said first and second plurality of electrodes contact the body and enable rapid electrical connection thereto for diagnostic testing, wherein said flexible strap comprises layers of flexible material formed with slots therein, each of said slots having a contact being movable therein in adjustable fashion, said strap being vertically adjustable, enabling said contact to be placed in an optimal location against the body.

2. The electrode system of claim 1 wherein said chair comprises a seat and seat back pivotably attached thereto, and a foot rest pivotably attached to said seat, said seat back and foot rest being adjustable into seated and reclining positions.

3. The electrode system of claim 1 wherein each of said second plurality of electrodes comprises a base containing an absorbent pad disposed under an electrically-conductive surface having holes formed therein, said pad containing an electrically-conductive liquid, to insure good contact with the skin.

4. The electrode system of claim 1 wherein said support structure means is provided with a cable receptacle connected to said electrodes enabling connection via a multi-wire cable to an EKG machine.

5. The electrode system of claim 1 further comprising an exerciser means having additional, alternative ones of said second plurality of electrodes mounted thereon, said exerciser means being removably attachable to said support structure means for enabling exercising of at least one of the arms and legs, providing stress conditions for testing.

6. The electrode system of claim 1 for use with self-administered diagnostic testing apparatus, said testing apparatus comprising a communication terminal mounted on said support structure means, said communication terminal automatically feeding a set of diagnostic test results to a central clinic.

7. The electrode system of claim 1 wherein said support structure means is a bed and further comprising a set of quick-release clamps, wherein said first plurality of electrodes enclosed in said flexible strap is removably attached at one end thereof to said bed by said quick-release clamps, and said second plurality of electrodes are each attached to said bed in removable fashion by said quick-release clamps.

8. The electrode system of claim 1 wherein said first plurality of electrodes comprises defibrillator electrodes.

9. The electrode system of claim 1 further comprising an echo transducer mounted in said flexible strap for performing echocardiograph tests.

10. A method for reducing the set-up time for placement of electrodes on parts of the body in medical diagnostic testing (EKG) comprising the steps of:
    providing a support structure means for supporting the body, having a first plurality of electrodes supported by said support structure means, said first plurality of electrodes being enclosed in a flexible strap attached at one end thereof to said support structure means, for placement of said flexible strap across the chest, and a second plurality of electrodes each fixedly mounted at a location on said support structure means for contacting the arms and legs; and
    supporting the body by said support structure means, such that said first and second plurality of electrodes contact the body and enable rapid electrical connection thereto for diagnostic testing,
    wherein said flexible strap comprises layers of flexible material formed with slots therein, each of said slots having a contact being movable therein in adjustable fashion, said strap being vertically adjustable, enabling said contact to be placed in an optimal location against the body.

11. The method of claim 10 further comprising the step of providing a self-administered diagnostic testing apparatus comprising a communication terminal mounted on said support structure means, and further comprising the step of performing the diagnostic test and obtaining a set of diagnostic test results, which are fed automatically to a central clinic via said communication terminal.

12. The method of claim 10 further comprising the step of attaching exerciser means to said support structure means for exercising at least one of the arms and legs while performing the test, to obtain complete EKG test results under stress conditions, said exerciser means having additional, alternative ones of said second plurality of electrodes mounted thereon.

13. The method of claim 10 wherein said support structure means is a chair for seating the body.

14. The method of claim 13 further comprising the step of attaching exerciser means to said support structure means for enabling exercising of at least one of the arms and legs, providing stress conditions for testing, said exerciser means having additional, alternative ones of said second plurality of electrodes mounted thereon, and
    providing an echo transducer retained in position within said flexible strap to contact the body and allow echocardiograph testing under said stress conditions.

15. The method of claim 10 wherein the step of providing a supporting structure comprises providing a bed upon which the body lies, and further comprising a set of quick-release clamps, wherein said first plurality of electrodes enclosed in said flexible strap is removably attached at one end thereof to said bed by said quick-release clamps, for placement of said flexible strap across the chest, said second plurality of electrodes being mounted on said bed in removable fashion by said quick-release clamps for contacting the arms and legs.

16. The method of claim 10 wherein said first plurality of electrodes comprises defibrillator contacts for use in a defibrillation treatment to administer electrical shock quickly.

17. An electrode system for reducing the set-up time for electrode placement on parts of the body in medical diagnostic testing (EKG) comprising in combination:
    support structure means for supporting the body;
    a first plurality of electrodes supported by said support structure means, wherein said first plurality of electrodes is enclosed in a flexible strap attached at one end thereof to said support structure means, for placement of said flexible strap across the chest, said flexible strap comprising layers of flexible material formed with slots therein, each of said slots having a contact being movable therein in adjustable fashion, said strap being vertically adjustable, enabling said contact to be placed in an optimal location; and
    a second plurality of electrodes each fixedly mounted at a location on said support structure means, said second plurality of electrodes being mounted for contacting the arms and
    such that when the body is supported by said support structure means, said first and second plurality of electrodes contact the body and enable rapid electrical connection thereto for diagnostic testing.

18. The electrode system of claim 17 wherein said support structure means is a chair for seating the body.

* * * * *